US006713246B1

(12) United States Patent
Reinecke et al.

(10) Patent No.: US 6,713,246 B1
(45) Date of Patent: Mar. 30, 2004

(54) METHOD OF PRODUCING INTERLEUKIN-1 RECEPTOR ANTAGONIST IN A SYRINGE FILLED WITH BLOOD

(75) Inventors: Julio Reinecke, Köln (DE); Hans Meijer, Köln (DE); Peter Wehling, Düsseldorf (DE)

(73) Assignee: Orthogen AG, Dusseldorf (DE)

( * ) Notice: Subject to any disclaimer, the term of this patent is extended or adjusted under 35 U.S.C. 154(b) by 0 days.

(21) Appl. No.: 09/890,723

(22) PCT Filed: Jan. 31, 2000

(86) PCT No.: PCT/EP00/00762

§ 371 (c)(1),
(2), (4) Date: Aug. 1, 2001

(87) PCT Pub. No.: WO00/46249

PCT Pub. Date: Aug. 10, 2000

(30) Foreign Application Priority Data

Feb. 1, 1999 (DE) .......................... 199 03 876

(51) Int. Cl.$^7$ .......................... A01N 1/02; A61M 37/00; A61M 1/00; A61B 19/00; C07K 7/00; C07K 1/00
(52) U.S. Cl. .......................... 435/2; 530/300; 530/350; 604/4.01; 604/6.07; 604/6.15; 604/317; 604/403
(58) Field of Search .......................... 530/300, 350; 604/4.01, 6.07, 6.15, 317, 403; D24/130

(56) References Cited

U.S. PATENT DOCUMENTS

| 5,075,222 A | * 11/1991 | Hannum et al. ............ 435/69.1 |
| 5,508,262 A | * 4/1996 | Norman, Jr. ................... 514/8 |
| 5,773,285 A | 6/1998 | Park |
| 5,972,880 A | 10/1999 | Pelletier et al. |
| 6,096,728 A | * 8/2000 | Collins et al. ................. 514/62 |
| 6,294,170 B1 | * 9/2001 | Boone et al. ............ 424/134.1 |
| 6,326,198 B1 | 12/2001 | Emerson et al. |

FOREIGN PATENT DOCUMENTS

| AU | 739517 | 3/1999 |
| WO | WO 96/01890 | 1/1996 |

OTHER PUBLICATIONS

Tsai et al. (1992) Cytokine–Induced Differentiation of Cultured Nonadherent Macrophages. Cellular Immunology 144(1): 203–216.*
Arend (2002) The Balance Between IL–1 and IL–1Ra in disease. Cytokine and Growth Factor Reviews 13(4/5): 323–340.*
Stedman's Medical Dictionary (2002) Physicians' Desk Reference, Medical Economics Company Inc.*
Caron et al. (1996) Chondroprotective Effect of Interarticular injections of interleukin–1 receptor antagonist in experimental osteoarthritis: Suppression of collagenase–1 expression. Arthritis and Rheumatism 39(9): 1535–1544.*
Henderson et al. (1991) Inhibition of Interleukin–1 induced synovitis and articular cartilage proteoglycan loss in the rabbit knee by recominant human interleukin–1 receptor antagonist. Cytokine 3(3): 246–249.*
Andersen et al. (1995) IgG for intravenous use, autologous serum and plasma induce comparable interleukin–1 receptor antagonist liberation from human mononuclear cells: an in vitro phenomenon depending upon plastic adherence. Autoimmunity 22(2): 127–133.*
Larrick (1989) Native Interleukin 1 Inhibitors. Immunol. Today 10(2): 61–66.*
Poutsiaka et al. (2001) Production of interleukin–1 receptor antagonist and interleukin–1 beta by peripheral blood mononuclear cells is differentially regulated. Blood 78(5): 1275–1281.*
Bresnihan et al. (1998) Treatment of Rheumatoid Arthritis with recombinant human interleukin–1 receptor antagonist. Arthritis and Rheumatism 41(12): 2196–2204.*
Smeenk et al. (Apr. 1997) "Effects of four different methods of sampling arterial blood and storage time on gas tensions and shunt calculation in the 100% oxygen test." Eur. Respir. J. 10(4): 910–913.*
Arend et al. "Effects of Immune Complexes on Production by Human Monocytes of Interleukin 1 or an Interleukin 1 Inhibitor", Journal of Immunology, vol 134, pp. 3868–3875 (1985).
Eisenberg et al. "Primary Structure and Functional Expression from Complementary DNA of a Human Interleukin–1 Receptor Antagonist", Nature, vol. 343, p. 341 (1990).
Tylman et al. "Release of Interleukin–10 by Reinfusion of Salvaged Blood After Knee Arthroplasty", Intensive Care Med., vol. 27(8), pp. 1379–1384 (2001).
Vowels et al. "Extra Corporeal Phototheraphy" J. Invest Dermatol, vol. 98(5), pp. 686–692 (1992).
Hannum et al. "Interleukin–1 Receptor Antagonist Activity of a Human Interleukin–1 Inhibitor", Nature, vol. 343, pp. 337–340 (1990).
Flynn et al. (July 1994) "In Vitro Activity of Readily Available Household Materials Against HIV–1: Is Bleach Enough?" Journal of Acquired Immune Deficiency Syndromes 7(7): 747–753.
Scott et al. (Aug. 28, 1971) "Leakage of Oxygen from Blood and Water Sample Stored in Plastic and Glass Syringes." British Medical Journal 3(5775): 512–516.
Matthijs (March 1992) "Choosing the Correct Materials for Medical Syringes." Medical Device Technology 3(2): 36–39.

* cited by examiner

*Primary Examiner*—Gary Kunz
*Assistant Examiner*—Christopher James Nichols
(74) *Attorney, Agent, or Firm*—Dickstein Shapiro Morin & Oshinsky, LLP

(57) ABSTRACT

The present invention relates to a method for producing interleukin-1 receptor antagonists, a prophylatically or therapeutically effective protein. A syringe is filled with a body fluid and incubated. The prophylatically or therapeutically effective protein is then produced in the body fluid.

13 Claims, 14 Drawing Sheets

METHOD OF PRODUCING INTERLEUKIN-1 RECEPTOR ANTAGONIST IN A SYRINGE FILLED WITH BLOOD

This application is a 371 of PCT/EP00/00762 filed Jan. 31, 2000 which claims priority to GERMANY 199 03 876.7 filed Feb. 1, 1999.

FIELD OF THE INVENTION

The present invention relates to a method for producing prophylactically or therapeutically active proteins and to the means employed therefor, in particular syringes.

BACKGROUND OF THE INVENTION

Therapeutically active proteins such as erythropoietin, insulin or interferons have been known for a long time. Many of these proteins have already been approved as medicaments and are accordingly employed frequently. Because of the large costs associated with the development and approval of these medicaments, however, there is a need for simple and cost-effective alternatives for the preparation of therapeutically active proteins. In addition, not all therapeutically active proteins are approved as medicaments. Nevertheless, however, there is frequently a need for these proteins also to be administered to the patient. Particularly important in this connection, because they are presumed to be well tolerated by the body, are autologous proteins, that is to say those intrinsic to the body. These proteins include the interleukin 1 receptor antagonist, interleukin 4, interleukin 10 and the type I or type II tumor necrosis factor receptor. Proteins intrinsic to the body moreover have the advantage that the natural post-translational modifications such as glycosylations are already present. This is not the case with most normally obtainable recombinant proteins because they are produced in prokaryotic hosts.

Stimulation of monoctyes by adherent immunoglobulin G to form the interleukin 1 receptor antagonist is described by Arend and Leung in Immunological Reviews (1994) 139, 71–78 and Moore et al. in Am. J. Respir. Cell Mol. Biol. (1992) 6, 569–575. Andersen et al. in Autommunity (1995) 22, 127–133 explains that the therapeutic effect of immunoglobulin G to be observed in vivo cannot be attributed to an enhanced formation of interleukin 1 receptor antagonist, and that the in vitro formation of the interleukin 1 receptor antagonist (IRAP, IL-1Ra) by monocytes depends on serum and plasma constituents adsorbed on polypropylene. The therapeutic use of adsorbed serum and plasma constituents to stimulate the formation of therapeutically interesting proteins in therapies is not only very costly but also involves the risk of contamination with infectious particles with which the serum and plasma constituents may be contaminated. Methods for producing IL-1Ra which can be employed directly in the therapy without using adsorbed serum and plasma constituents are not described in the aforementioned publications.

The technical problem on which the present invention is based is thus to provide methods and means for producing IL-1Ra which serve as safe, cost-effective alternatives which can be carried out quickly for the use and for the production of conventional pharmaceutical products.

The invention solves this problem by providing a method for producing IL-1Ra in a syringe made of glass, quartz or a plastic, the syringe being filled with a body fluid from an organism, for example a human or animal body, and incubated, and the IL-1Ra being formed.

BRIEF SUMMARY OF THE INVENTION

A preferred embodiment of the present invention provides for the internal structure of the syringe to consist of a special material, in particular a glass, plastic, quartz and/or corundum, whose surface is, in a particularly preferred embodiment of the invention, modified, in particular with the aid of a corrosive agent, for example an acid or an alkali, in particular chromosulphonic acid, and subsequently, after removal of the agent and washing the syringe where appropriate, that is to say in a particularly preferred manner, the surface of the internal structure of the syringe is sterilized, in particular by autoclaving. The syringe is then filled with a patient's body fluid and incubated, and IL-1Ra is formed thereby. The body fluid enriched with the protein can then be reinjected into the patient, for example into a diseased joint. However, to increase the purity of the IL-1Ra which has been formed, the body fluid is preferably centrifuged and the supernatant is sterilized by filtration, divided into aliquots and stored for a later treatment. The invention thus provides in a preferred embodiment in a first step of the method for the surface of the internal structure of the syringe to be modified, in particular with the aid of a corrosive agent, such as an acid or an alkali, in particular chromosulphonic acid, and then, if desired, the surface of the internal structures of the syringe is sterilized, in particular by autoclaving. A drying can be provided before and/or after the sterilization. After the modification and the sterilization which takes place where appropriate, the syringe is filled in a second step of the method with a body fluid, in particular blood, lymph, saliva or urine, and incubated. The body fluid is preferably taken from the patient directly with the syringe. The, preferably modified, surface of the internal structure of the syringe induces in the body fluid specifically, to an extent which differs quantitatively depending on the material employed, the internal structure of the syringe, modification employed, in particular etching of the internal structure, sterilization employed, in particular autoclaving, and body fluid employed, the formation of IL-1Ra which, accordingly, becomes enriched or is formed in the body fluid present in the syringe. The body fluid enriched in this way can be stored sterile in the syringe and be returned to the patient as required directly without further treatment or, preferably, after centrifugation and/or sterilization by filtration.

The invention thus also relates to a method for the prophylactic or therapeutic treatment of the human or animal body, for example for the treatment of rheumatism, osteoarthritis and/or back symptoms, wherein a body fluid, for example blood, is taken from the human or animal body by means of a syringe according to the present invention, this body fluid is incubated in the syringe, and IL-1Ra is formed or enriched thereby, and the body fluid is returned using this syringe to the same or a different human or animal body.

The IL-1Ra which is formed can advantageously be modified, for example glycosylated. It is self-evident that the invention also encompasses the formation of other modifications or variants of IL-1Ra, such as truncated forms, mutants or other derivatives.

In conjunction with the present invention, an internal structure of a syringe means any region or any structure of the syringe which is present in its interior, that is to say in the sample reception region and may come into contact with the body fluid to be received. The internal structure of a syringe is particularly advantageously its inner surface, preferably a surface with a texturing to increase the surface area. It is self-evident that the present invention can also be carried out using a commercially available syringe without a special configuration in its internal cavity. In such a case the internal structure is the inner surface of the syringe barrel and the part of the piston present in the barrel. The internal structure can, in a particularly preferred embodiment, additionally be formed by articles introduced into the interior of the syringe, such as particles, spheres, beads, gels, glass wool, corundum, quartz, sand, plastic or glass granules or powder or the like in order to enlarge the internal surface area of the syringe and thus provide a larger inducing surface. The material of which the internal structure consists or which is present in the internal structure can be a material different from that of which the remainder of the syringe consists. For example, the syringe may consist of plastic and parts of its internal structure may, for example, consist of glass granules.

Additional structures of these types, such as, for example, glass beads with a diameter of from 1 to 5 mm, should, according to a preferred embodiment of the invention, however occupy not more than 50% of the internal volume of the syringes employed. The syringes employed may be, for example, 10 to 100 ml syringes.

In connection with the present invention, a modified surface of an internal structure of the syringe means a surface which has been treated with a corrosive agent and which is capable of inducing and/or enhancing the formation of IL-1Ra in a body fluid of a human or animal. The modified surface may be distinguished by a particularly great cleanliness, that is to say substantial or complete absence of contaminants and/or a chemical/physical modification of the surface properties and/or structure. The modified surface of the internal structure is preferably produced by employing an alkali or an acid, for example chromosulphonic acid, in particular 20 to 80% strength, particularly preferably 50% strength, chromosulphonic acid. The syringe is preferably incubated with the corrosive agent, in particular the chromosulphonic acid, for 5 to 30 min.

After removal of the agent it is possible and preferred to carry out one or more washing steps and, where appropriate, preferably a sterilization, for example by autoclaving, in particular autoclaving at 100° C. to 150° C. for 20 to 60 min under a pressure of from 1 to 5 bar. After the washing and before and/or after the autoclaving it is possible where appropriate also for one or more drying steps to take place at 60 to 150° C., preferably 80° C., for 30 to 120 min in, for example, a drying oven.

A particularly advantageous configuration of the invention provides for the syringe, in particular the internal structure of the syringe, to be produced from glass, for example quartz glass, corundum, quartz, a plastic such as polystyrene, polyethylene, polyvinyl chloride, polypropylene, or a similar material, that is to say consists of these materials or essentially comprises these materials or mixtures thereof.

It has surprisingly been possible to show within the framework of the present teaching that a syringe made of glass, and/or an internal structure made of glass, in particular glass granules, displays a particularly strongly inducing effect.

In a particularly preferred embodiment, heated glass is used before the treatment, that is to say before removal of the body fluid, in particular glass which has been heated to 100° C.–210° C., in particular 170°–200° C., preferably 180° C., and which is, of course, cooled before the use according to the invention. In a particularly preferred embodiment, the glass can be in the form of glass powder or glass granules.

The internal structures may, however, also consist of quartz, for example quartz powder or quartz sand and/or corundum, for example in the form of a suspension in water, or comprise the latter.

In a particularly preferred embodiment, these materials display IL-1Ra-inducing properties after modification, in particular etching, has taken place where appropriate and after the sterilization has taken place where appropriate.

A further preferred embodiment of the invention provides for the internal structure of a syringe to be provided with a coating which can be modified and can be sterilized, and for the modification and, where appropriate, the sterilization to be carried out subsequently.

The present invention is advantageous inasmuch as it provides a method which is simple to carry out and with which it is possible to produce autologous IL-1Ra which can be produced by induction, in particular surface induction, and can, in the form thus produced, that is to say together with the other constituents of the fluid present in the syringe, be readministered to the patient directly, that is to say without further manipulation such as, for example, transfer into another container. In a preferred embodiment, a centrifugation and/or sterilization by filtration can be provided to remove solid constituents before the IL-1Ra which has been formed is administered. The use of commercially available, often costly, medicaments thus becomes redundant. Finally, the invention proves to be advantageous since it avoids contamination, pollution, infection or the like of the IL-1Ra which derives from a medicament production taking place outside the patient.

The present invention thus provides in a particularly preferred embodiment a method for producing the interleukin 1 receptor antagonist, where the internal structures of the syringe consist of a specially treated material, in particular glass, quartz or plastic, where the surface of the internal structures of the syringe has been modified, in particular with the aid of a corrosive agent, in particular chromosulphonic acid, where the surface of the internal structures of the syringe has, where appropriate, subsequently been sterilized, in particular by autoclaving, and where the syringe is filled with a body fluid, preferably blood, and incubated, and IL-1Ra is formed and enriched in the body fluid. Inter alia because of the special modification of the surface of the internal structures of the syringe, in particular etching, and the special sterilization of the surface, in particular autoclaving, the syringe of the invention is able to stimulate the monocytes present in the blood to form IL-1Ra so that the latter becomes enriched in the blood. The blood present in the syringe can, in one embodiment of the present invention, after incubation, that is to say after enrichment of the IL-1Ra, be returned to the patient from whom the blood introduced into the syringe was taken, directly, without further manipulation such as, for example, transfer.

It is possible and advantageous in a particularly preferred embodiment of the present invention to provide a centrifugation and/or sterilization by filtration of the blood present in the syringe in order to remove solid constituents such as cells. It is then divided into aliquots where appropriate. It is thus also provided by the invention that the blood can be taken from the patient by means of the syringe equipped with a specially modified and sterilized, in particular autoclaved, surface of the internal structures, the blood can be incubated in the syringe and, after formation of IL-1Ra, can be returned to the same patient or another one with the syringe. Such a procedure is particularly advantageous for example in the area of neuroorthopedics, that is to say, for example, for back symptoms with a neurological causation. Suitable treatment for such symptoms to date has been only an intervertebral disk operation, cortisone treatment, irrigations with saline solutions or the like. The provision by the invention of IL-1Ra, that is to say, in particular, autologous IL-1Ra, also makes treatment of rheumatism and osteoarthritis possible in a particularly simple, cost-effective and efficacious way.

The invention provides in another embodiment for the internal structure of the syringe additionally to be coated with anticoagulants, in particular heparin, citrate, EDTA, CPDM or CPDA. It has surprisingly been possible to show within the framework of the present teaching that a good induction is achieved on use of heparin as anticoagulant. It is also possible to provide according to the invention for the anticoagulants to be employed not as coating but unbound in the container, for example put in the lyophilized or liquid state into the syringe.

However, in a particularly preferred embodiment of the present invention, no anticoagulant, in particular no heparin, is employed in the syringe. This leads to a further improvement in the incubation.

The invention provides in a further preferred embodiment for the incubation of the body fluid in the syringe to be carried out over a period of from 12 to 72 hours, preferably 24 hours, preferably at room temperature, that is to say 20° C. to 41° C., in particular at 37° C.

The invention also provides in one configuration of the invention for the body fluid to be treated further after formation of the therapeutically or prophylactically active protein in the body fluid, in order, for example, to remove particular constituents of the latter, for example blood plasma or blood platelets. This removal can in a preferred embodiment of the invention be carried out by centrifugation or filtration.

The invention relates in a further embodiment to a method for producing a syringe which is suitable for the in vitro induction of prophylactically or therapeutically active proteins, in particular the interleukin 1 receptor antagonist, where the syringe is distinguished by the specially treated material of the internal structure of the syringe, in particular plastic or glass. The invention provides in particular for the surface of the internal structure of the syringe to be etched by a corrosive agent, in particular an alkali or an acid, in particular using chromosulphonic acid. After removal of the corrosive agent and washing of the syringe it can be provided for the surface of the internal structure to be sterilized, in particular autoclaved. It can preferably also be provided for a syringe, preferably produced from glass, to be heated before use thereof, for example to 100° C. to 210° C., in particular 170°–200° C.

The invention of course also relates to the syringe produced in this way, which, in a particularly preferred embodiment, is produced from glass, quartz or plastic, in particular polystyrene, polyvinyl chloride, polyethylene or polypropylene, where the syringe is distinguished by the special treatment of the surface of the internal structure of the syringe, in particular produced from glass, quartz or plastic, which is carried out by exposure to a corrosive agent. In a preferred manner, the syringe has been heated before use thereof, preferably to 100° C.–210° C., for example 170° C.–200° C.

The invention also relates to the use of alkali or acid, in particular chromosulphonic acid, for modifying the surface of the internal structures of the syringes of the invention, preferably made of polystyrene, polyvinyl chloride, polyethylene, polypropylene, quartz or glass, for the in vitro induction of prophylactically or therapeutically active proteins, preferably the interleukin 1 receptor antagonist.

The invention also relates to the use of devices or substances which enlarge the surface area, such as glass powder, glass granules, quartz powder, quartz sand, corundum, spheres, beads, sand and so forth for use in an aforementioned method, that is to say in particular for use as inducer of IL-1Ra formation in a vessel, for example a syringe.

Further advantageous configurations of the invention are evident from the dependent claims.

The invention is illustrated in detail by means of figures and exemplary embodiments.

DETAILED DESCRIPTION OF THE INVENTION

EXAMPLE 1

Production and Use of a Glass Syringe with Granules

Figure 1:
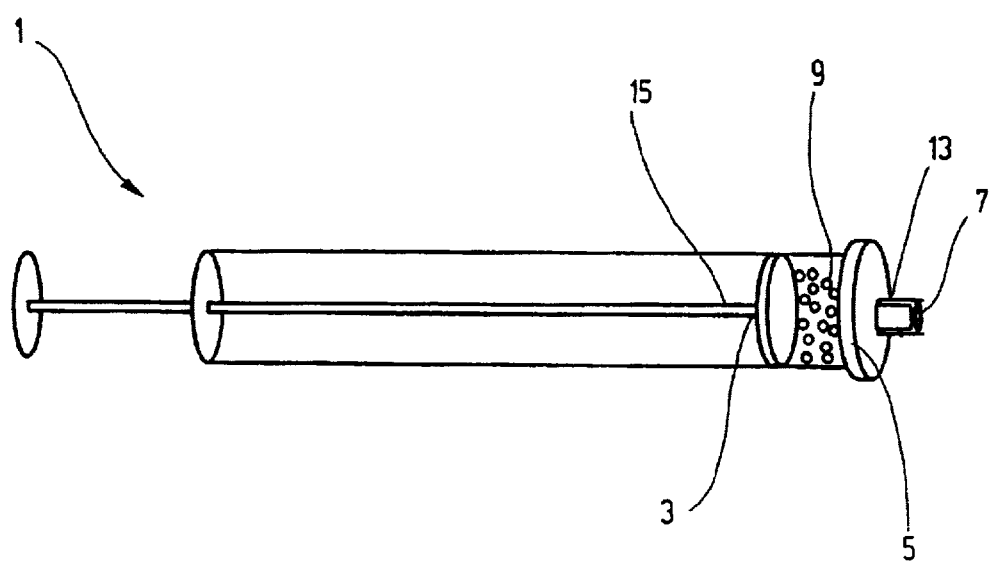
FIG. 1 shows a diagrammatic representation of a syringe of the invention.

FIG. 1 shows a 50 ml syringe 1 made of glass (Fortuna Optima, Order No. 7.102.-44, unless indicated otherwise hereinafter, this syringe was employed in all the examples) with a piston or plunger 3, with a closure 5 which can be unscrewed and has a closure attachment 13 (male Luer) and with a removable cap 7 which is disposed on the closure attachment 13 and closes the latter and has a septum. The plunger 3 has a predetermined breaking point 15. It is thus possible to centrifuge the syringe directly after breaking off the plunger. Glass granules 9 (glass beads from Roth, Art. No. A 557.1) are also depicted. The size of the particles of the granules 9 is between 1 and 3 mm in diameter, it also being possible, however, to employ smaller particles, in particular larger than 100 μm, for example glass powder. It is, of course, also possible to employ syringes, for example made of glass or plastic, which have no predetermined breaking point in the plunger.

The syringe 1 is produced by modifying the surface of the internal structure of the syringe 1 which is new ex-factory and in its original pack and of the granules 9 which are new ex-factory and in their original pack with the aid of a commercially available chromosulphonic acid product by taking the chromosulphonic acid product into the syringe and etching the inner wall of the syringe, that is to say inner wall of the barrel and piston, and the granules, therewith. The syringe is treated, and thus cleaned and modified, by 50% strength chromosulphonic acid (Merck, Darmstadt, Order No. 1.02499.2500, chromosulphonic acid is diluted with Biochrom ultrapure water No. L 0040 to the desired dilution) being completely drawn up and ejected one to ten times, preferably three times. After the last drawing up, the syringe is sealed at the bottom and incubated in the state filled with chromosulphonic acid for 5 to 30 min. The syringe piston is then removed and thoroughly washed two to ten times, preferably four times, by complete filling and draining of the syringe barrel with fresh ultrapure water, it being necessary to take care that filling and emptying of the washing water is complete. The syringe piston is then immersed in 50% strength chromosulphonic acid and thoroughly washed with distilled water.

Any residues of water present in the syringe are removed by capillary suction by swabbing the Luer connector in order to ensure rapid drying of the syringe. Pistons and syringes including any glass beads present therein are separately sealed (Melag, Melaseal) in Melag film with indicator field (Melag, Melafol 1502). The syringes packed in this way are dried in a drying oven (Melag drying sterilizer) at 80° C. for at least 60 min. The dried, packed syringes are then autoclaved at 132° C. under 2 bar for 30 min (Wolf Autoclave HRM 242 II) and dried once more at 80° C. for at least 60 min.

Before the removal of blood (see below), heparin (Liquemin N 2500, heparin sodium 2500 I.U.) or citrate (ACDA) is introduced into the syringe in order to prevent coagulation of the blood taken up later. The use of coagulants may prove to be advantageous in the processing of IL-1Ra containing serum.

The syringe 1 is employed by removing blood from a patient with the aid of an adapter which is not depicted and which connects the cap 7 which can be unscrewed by means of a tubing, which is not depicted, to a cannula which is not depicted. The adapter has a needle by means of which the septum present in the closure attachment 13 is pierced. The adapter is then removed and the whole blood is incubated at 37° C. for 24 hours under the protection of the removable cap 7, whose septum has closed automatically. The incubation can take place vertically or horizontally. If the incubation takes place vertically, the plasma is removed through the septum and a sterile fitted filter (0.2 μm). In addition or alternatively, a centrifugation can be provided. If the incubation takes place horizontally, the blood is centrifuged and the plasma is removed through a sterile fitted filter (0.2 μm). However, it is also possible to provide for the plasma to be removed through the septum without carrying out a centrifugation. The plasma is then, for example, reinjected into a nerve root or a joint of the patient.

EXAMPLE 2

Production and Use of a Plastic Syringe with Granules

In this example, there is use of sterile granules made of polystyrene, glass or another modifiable and/or sterilizable material. The surface of the granules is modified using a commercially available chromosulphonic acid product in the batch method as stated in example 1. The granules are then rinsed with water in order to wash off the residues of chromosulphonic acid. The granules are then incubated at 121° C. under a pressure of 2 bar for at least 20 min so that the granules are sterilized and saturated with water. The granules are then dried at 80° C. for 20 min.

A conventional, unmodified polypropylene syringe new exfactory and in the original pack (50 ml, Becton Dickinson, Heidelberg, Art. No. 00137) is charged with the modified and sterilized granules (1, 2, 4 or 10 cm3) and with a sufficient amount of an anticoagulant such as heparin (Liquemin, heparin sodium 2500 I.U.) or citrate (for example ACDA).

The charged syringe, including removal cannula and tubing, is packaged and then sterilized with gamma rays or electrons.

The user removes the sterile kit and removes blood from the patient. The syringe has on its orifice in the closure attachment a septum which, for the removal, is pierced by the removal accessory, that is to say the needle of the adapter. After removal of the adapter, the septum closes automatically again. After removal of blood, the syringe plunger is broken off at a predetermined breaking point.

The syringe with blood is incubated at 37° C. to 41° C. for 24 hours.

a) If the incubation takes place vertically, the plasma is removed through the septum and a sterile fitted filter, for example 0.2 μm.

b) If the incubation takes place horizontally, after centrifugation of the syringe the plasma is removed through a sterile fitted filter, for example 0.2 μm.

Reinjection of the plasma takes place, for example, at a nerve root, into the joint or into the intervertebral disk.

EXAMPLE 3

Production and Use of a Syringe without Granules

A syringe in the original pack, new ex-factory and made of a modifiable, sterilizable material (5, 10, 20 or 50 ml) is modified with chromosulphonic acid as indicated in example 1 and then autoclaved and dried. The syringe preferably consists of glass, polystyrene or a specially modifiable other material.

The modified and sterilized syringe is charged with a sufficient amount of heparin (Liquemin, heparin sodium 2500 I.U.) or citrate (ACDA). The charged syringe, including removal cannula and tubing, is packaged and then sterilized with gamma rays or electrons.

The user removes the sterile kit and removes blood from the patient. The syringe has on its orifice in the closure attachment a septum which, for the removal, is pierced by the removal accessory, that is to say the needle of the adapter. After removal of the adapter, the septum closes automatically again. After removal of blood, the syringe plunger is broken off at a predetermined breaking point.

The syringe with blood is incubated at 37° C. to 41° C. for 24 hours.

a) If the incubation takes place vertically (for example in a test tube holder), the plasma is removed through the septum, filtering through a sterile fitted filter, for example 0.2 μm.

b) If the incubation takes place horizontally, after centrifugation of the syringe the plasma is removed through the septum, filtering through a sterile fitted filter, for example 0.2 μm.

Reinjection of the plasma takes place, for example, at a nerve root, into the joint or into the intervertebral disk.

EXAMPLE 4

Production of the Interleukin 1 Receptor Antagonist in a Syringe Using Heparin A commercially available glass syringe new ex-factory and in the original pack was filled with chromosulphonic acid and incubated at room temperature for 20 min as indicated in example 1. The syringe was then rinsed four times with distilled water, packaged, autoclaved at 131° C. under a pressure of 2 bar for 30 min and dried at 100° C. for 30 min.

After completion of the modification and sterilization, the syringe is stored for the time being. Heparin approved under the drugs legislation (Liquemin, heparin sodium 2500 I.U.) is drawn up into the syringe as anticoagulant.

The coated syringe is then used to take venous blood from the patient under sterile conditions.

The syringe is incubated at room temperature for 12 to 72 hours. During this time the proteins present in the plasma, in particular the interleukin 1 receptor antagonist, becomes highly enriched in the blood plasma. It was possible to find a concentration of from 1 to 50 ng/ml of the interleukin 1 receptor antagonist.

The blood or the plasma is then injected into the patient with the coated syringe.

EXAMPLE 5

Production of the Interleukin 1 Receptor Antagonist in a Syringe without Using Heparin A commercially available glass syringe new ex-factory and in the original pack was filled with chromosulphonic acid and incubated at room temperature for 20 min as indicated in example 1. The syringe was then rinsed four times with distilled water, packaged, autoclaved at 131° C. under a pressure of 2 bar for 30 min and dried at 100° C. for 30 min.

After completion of the modification and sterilization, the syringe is stored for the time being.

The coated syringe is then used to take venous blood from the patient under sterile conditions.

The syringe is incubated at room temperature for 12 to 72 hours. During this time the proteins present in the plasma, in particular the interleukin 1 receptor antagonist, becomes highly enriched in the blood plasma. It was possible to find a concentration of from 1 to 50 ng/ml of the interleukin 1 receptor antagonist.

The diluted blood or the culture supernatant is then injected into the patient.

EXAMPLE 6

Production of IL-1Ra in a Polystyrene Microtiter Plate with Granules

The granules are produced by modifying the granules new exfactory and in the original pack in the batch method with the aid of a commercially available chromosulphonic acid product by putting the granules in a container (such as, for example, a 250 ml glass beaker XXX) to which a 50% strength chromosulphonic acid product (Merck, Darmstadt, Order No. 1.02499.2500, chromosulphonic acid is diluted with Biochrom ultrapure water No. L 0040 to the desired dilution), and the granules are treated and thus cleaned and modified. The granules are incubated with the chromosulphonic acid for 5 to 60 minutes.

The chromosulphonic acid is then removed and the spheres are washed thoroughly two to ten times with fresh ultrapure water. Washing is continued until, in the penultimate washing step, the pH and the conductance of the ultrapure water and the washing water are identical.

The granules are then autoclaved in a glass beaker (such as, for example, a 250 ml glass beaker XXX) at 132° C. under 2 bar for 30 min (Wolf Autoclave HRM 242 II) and dried at 60° C. to 100° C., preferably at 80° C., for 30 min. Alternatively, the granules are heat-sterilized (Melag dry sterilizer) directly at 120° C. to 210° C., preferably at 180° C., for 30 minutes.

The following are used for the removal of blood: Sarstedt monovettes with EDTA, citrate, CPDA, CPDM or heparin, in order to prevent coagulation of the blood taken up later.

Three to 12 glass beads are placed in each well of a microtiter plate (Nunc, Art. No. 150 687), and 1 ml of blood is added as quickly as possible after removal.

After incubation (37° C., 5% CO2) for 24 h (Hereaus incubator):

blood clot sediments overnight, and 300 µl of serum are removed, without disturbing or picking up solid constituents, and the IL-1Ra protein concentration is determined (ELISA, R&D, Wiesbaden, Quantikine Human IL-1Ra).

Figure 2:
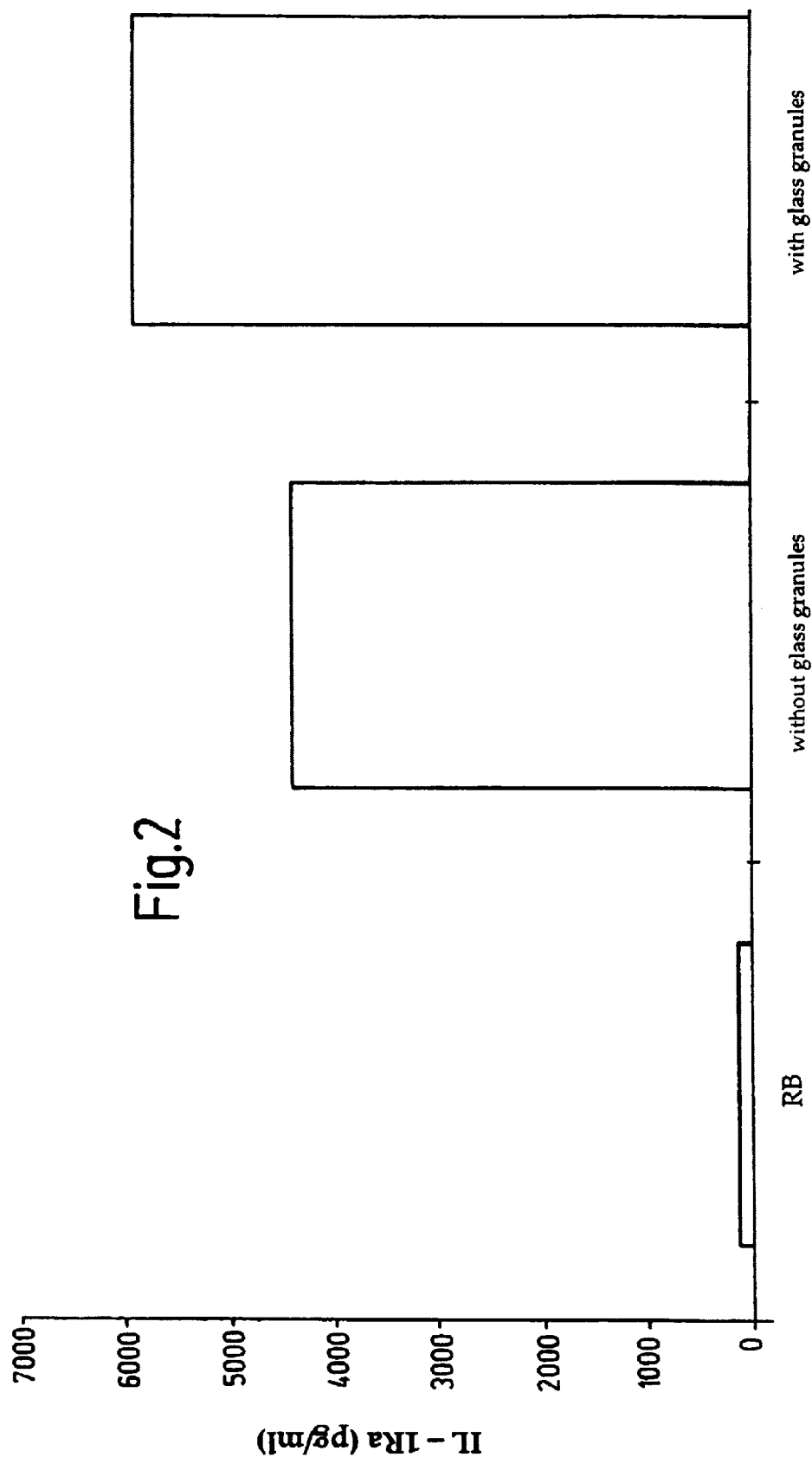
FIGS. 2 to 12 show the formation of IL-1Ra in a syringe employed according to the invention under various conditions.

FIG. 2 is a bar graph IL-1Ra production in a glass syringe with and without glass granules. IL-1Ra level in picograms per milliliter is shown on the Y axis, plus or minus standard error. The bars on the X-axis show IL-1Ra levels for the (1) Reaction Blank (RB), (2) without glass granules, and (3) with glass granules.

Method

IL-1Ra production

Use of a glass syringe as described in example 1 Measurements on a patient

Glass spheres

Roth, treated with chromosulphonic acid, washed and autoclaved

RB

Reaction blank, IL-1Ra concentration on removal (before IL-1Ra production)

Result

Addition of the glass granules increases IL-1Ra production.

Figure 3:
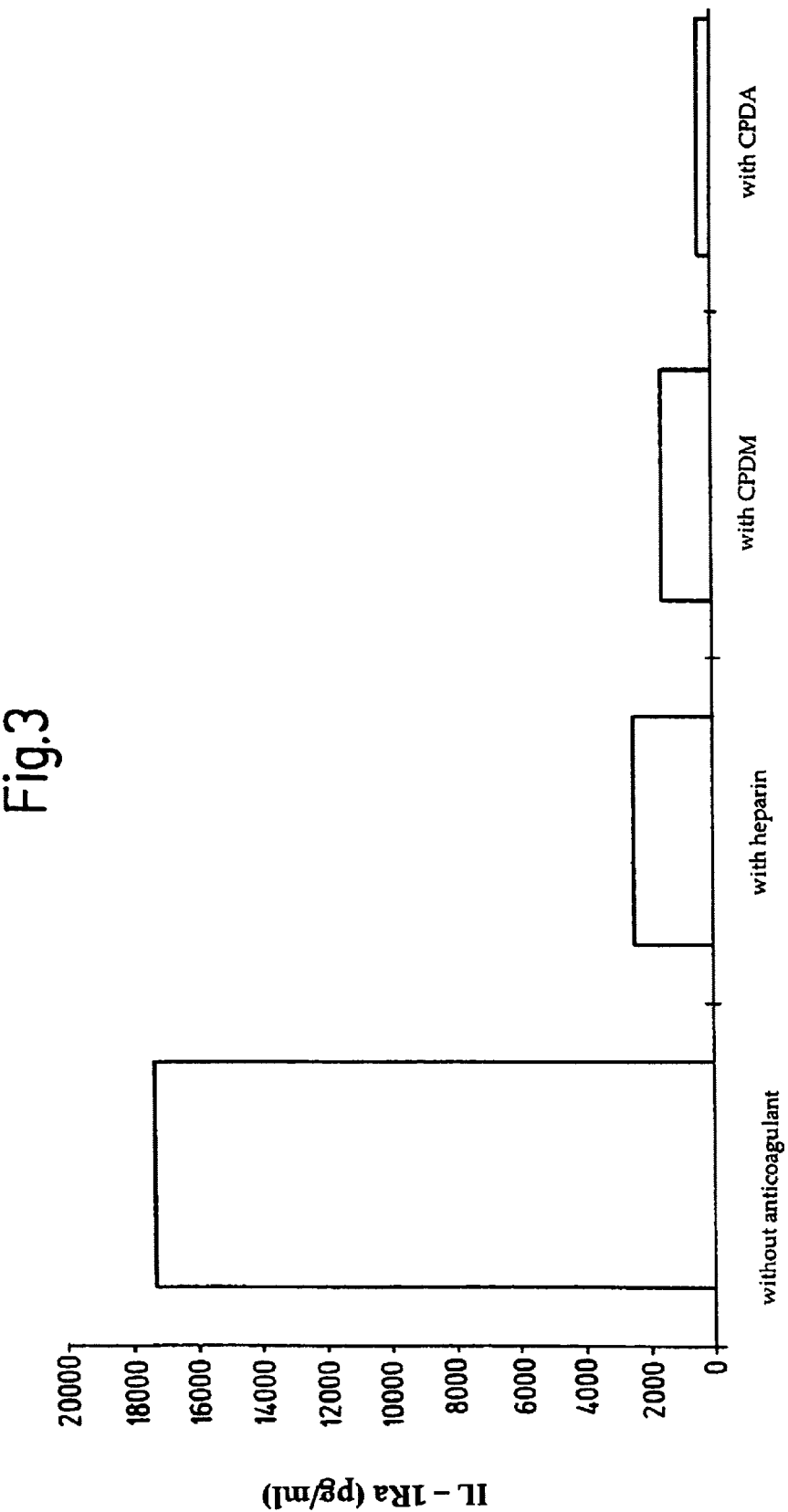

FIG. 3 is a bar graph showing IL-1Ra production in a glass syringe with and without anticoagulant. The Y-axis shows the level of IL-1Ra in picograms for milliliter, plus or minus standard error. The bars on the X-axis show IL-1Ra levels (1) without anticoagulant, (2) with heparin, (3) with CPDM, and (4) with CPDA as dicussed below.

Method

IL-1Ra production

Use of a glass syringe as described in example 1 Measurements on a patient

Glass spheres

Roth, treated with chromosulphonic acid, washed and autoclaved

CPDM citrate phosphate dextrose mannitol

CPDA citrate phosphate dextrose adenine

Result

Addition of various anticoagulants influences the efficiency of IL-1Ra production to varying extents.

Figure 4:
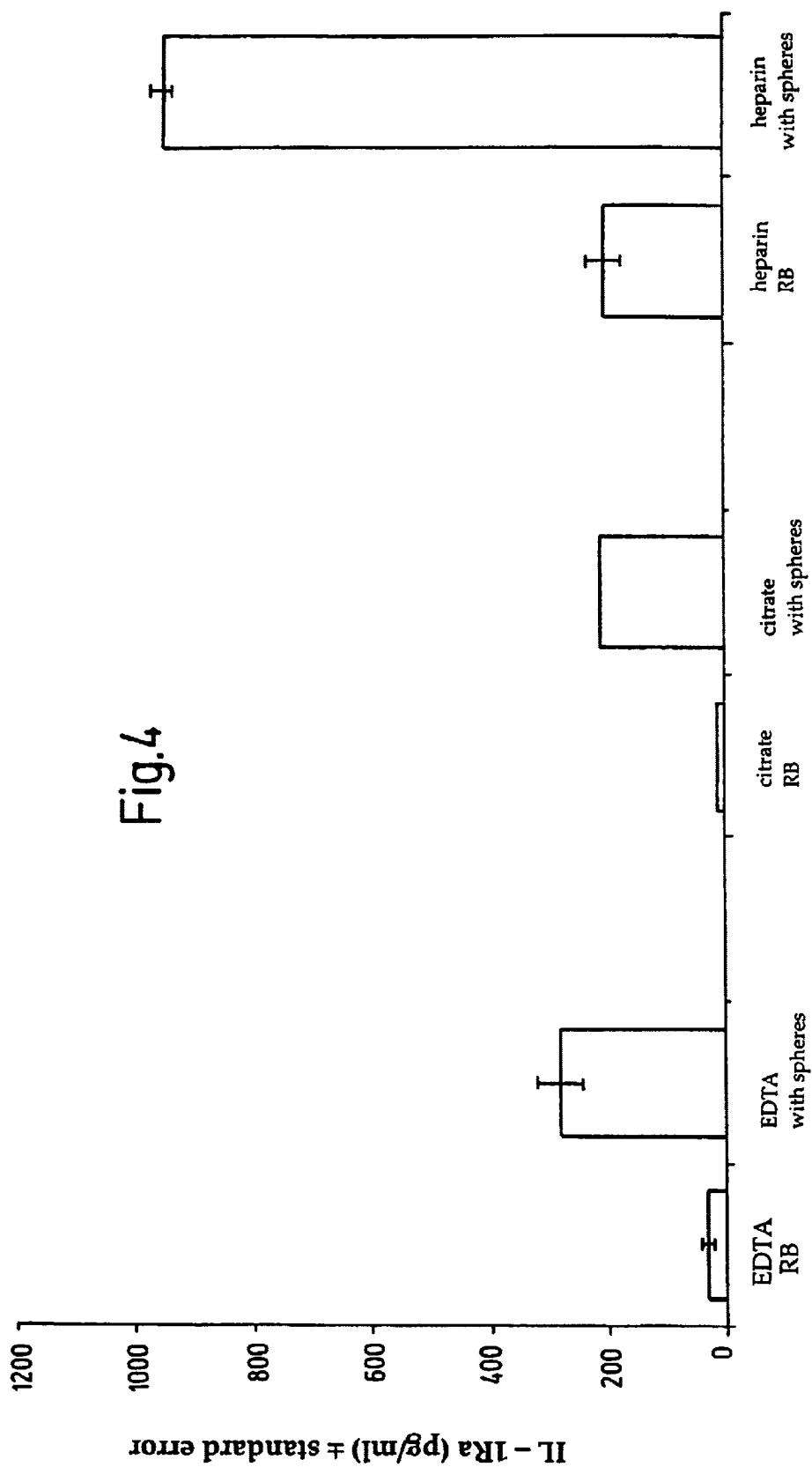

FIG. 4 is a bar graph showing IL-1Ra production in a microtiter plate with and without anticoagulant. IL-1Ra level in picograms per milliliter is shown on the Y axis, plus or minus standard error. The bars on the X-axis show IL-1Ra levels for (1) EDTA, EDTA with spheres, (2) citrate, citrate with spheres, and (3) heparin, heparin with spheres as discussed below.

Method

IL-1Ra production

Use of a microtiter plate as described in example 6 Measurements on a patient

Glass spheres

Duran, treated with chromosulphonic acid, washed and autoclaved. 12 spheres were added to 1 ml of whole blood

RB

Reaction blank, IL-1Ra concentration on removal (before IL-1Ra production)

Result

Addition of various anticoagulants influences the efficiency of IL-1Ra production to varying extents.

Figure 5:
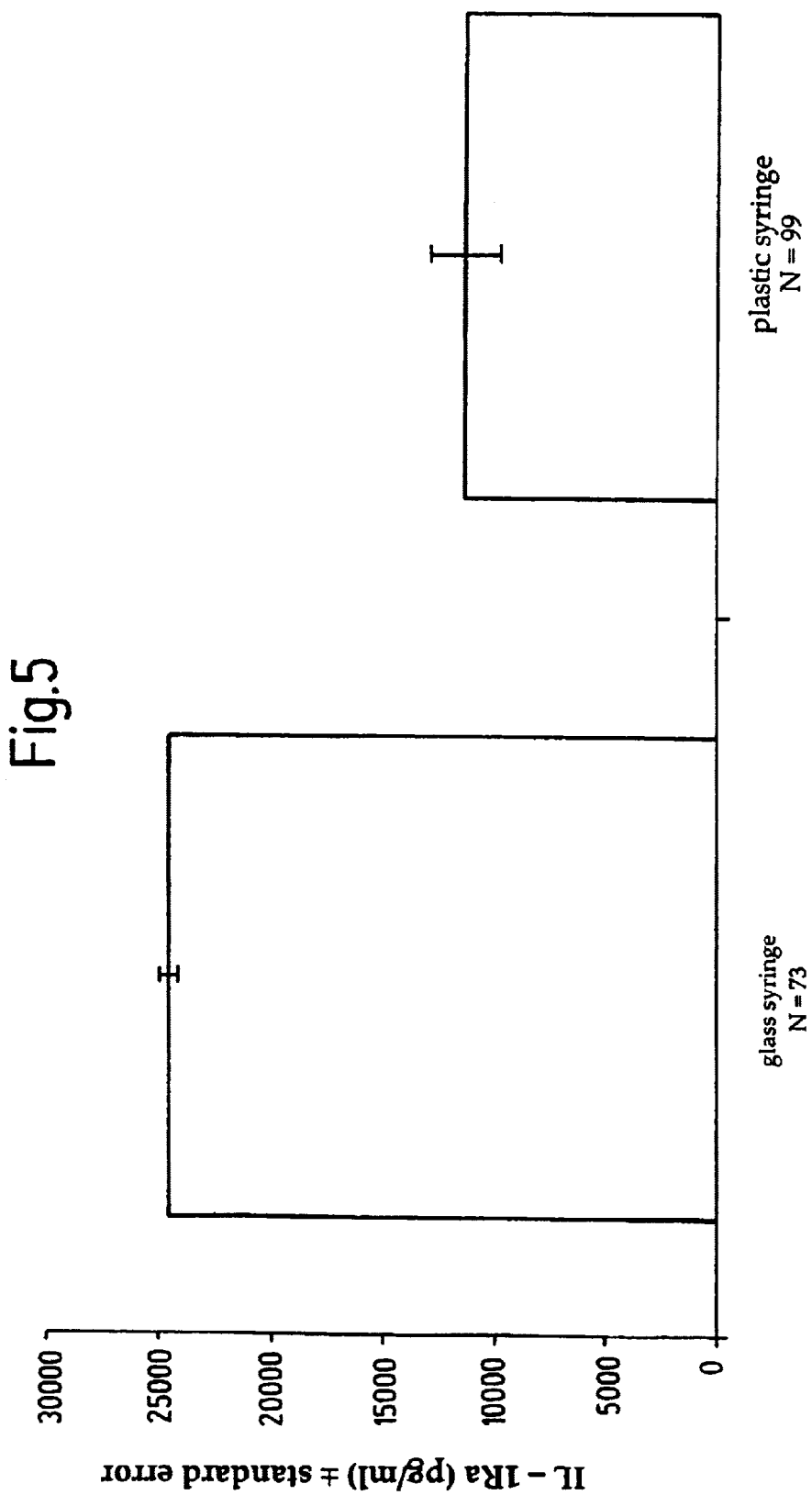

FIG. 5 is a bar graph showing IL-1Ra production in a glass and plastic syringe with glass granules in a group of patients. IL-1Ra level in picograms per milliliter is shown on the Y-axis, plus or minus standard error. The bars on the X-axis show IL-R1a levels for a glass syringe, N=73 and a plastic syringe, N=99 as discussed below.

Method
IL-1Ra production
Use of a glass syringe as described in example 1 and 2
    Measurements on a group of orthopedic patients
Glass spheres
Roth, treated with chromosulphonic acid, washed and
    autoclaved
Result
IL-1Ra can be produced in both a glass and a plastic syringe, but the efficiency of IL-1Ra production in a glass syringe is significantly higher.

Figure 6:
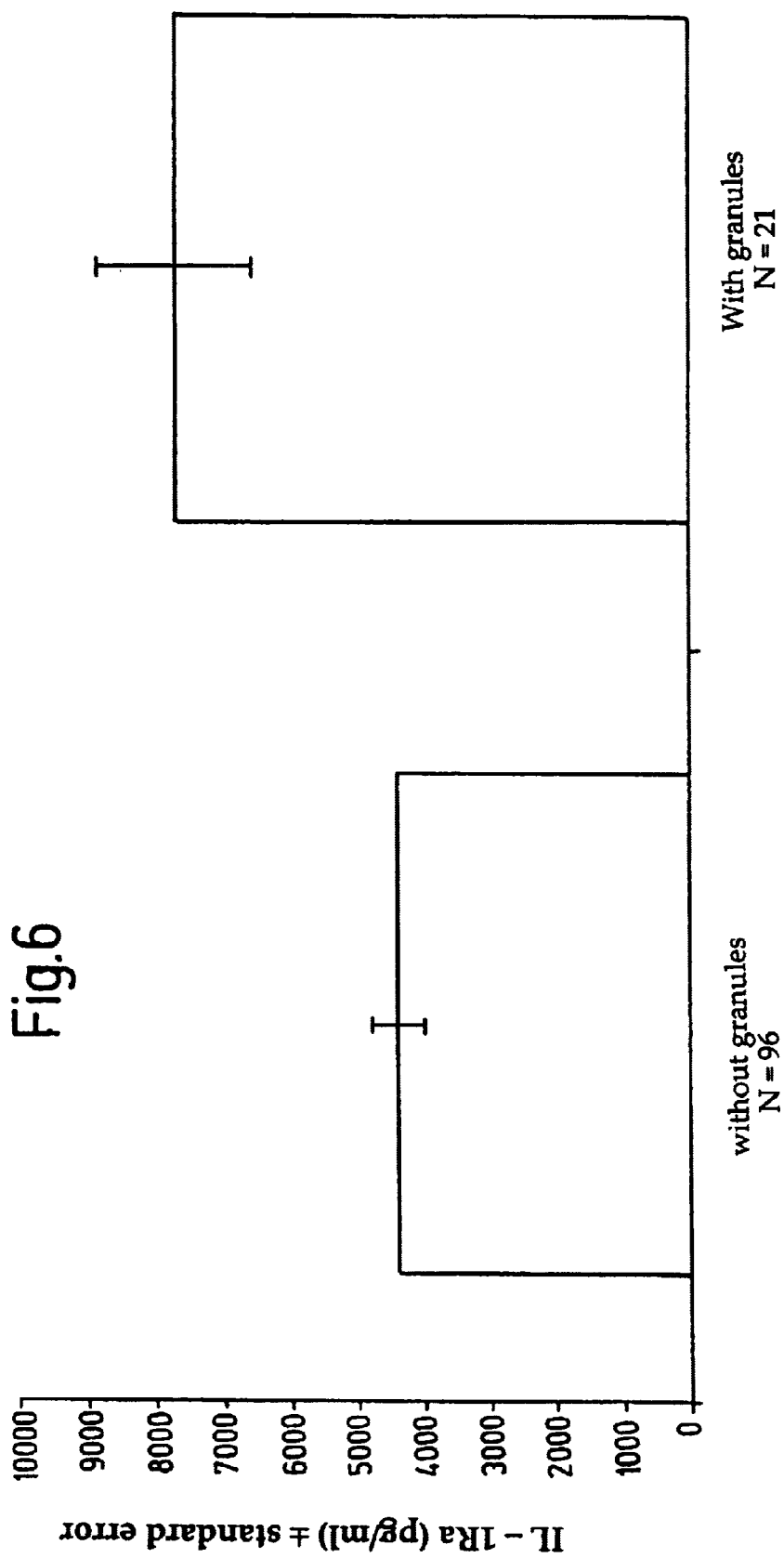

FIG. 6 is a bar graph showing IL-1Ra production in a glass syringe with and without glass granules in a group of patients. IL-1Ra level in picograms per milliliter is shown on the Y-axis, plus or minus standard error. The bars on the X-axis show IL-1Ra levels in (1) a glass syringe with granules, N=96 and (2) a glass syringe without granules, N=21 as discussed below.

Method
IL-1Ra production
Use of a glass syringe as described in example 1 Measurements on a group of orthopedic patients
Glass spheres
Roth, treated with chromosulphonic acid, washed and
    autoclaved
Result
IL-1Ra can be produced in a glass syringe both with and without glass granules, but the efficiency of IL-1Ra production with glass granules is significantly higher.

Figure 7:
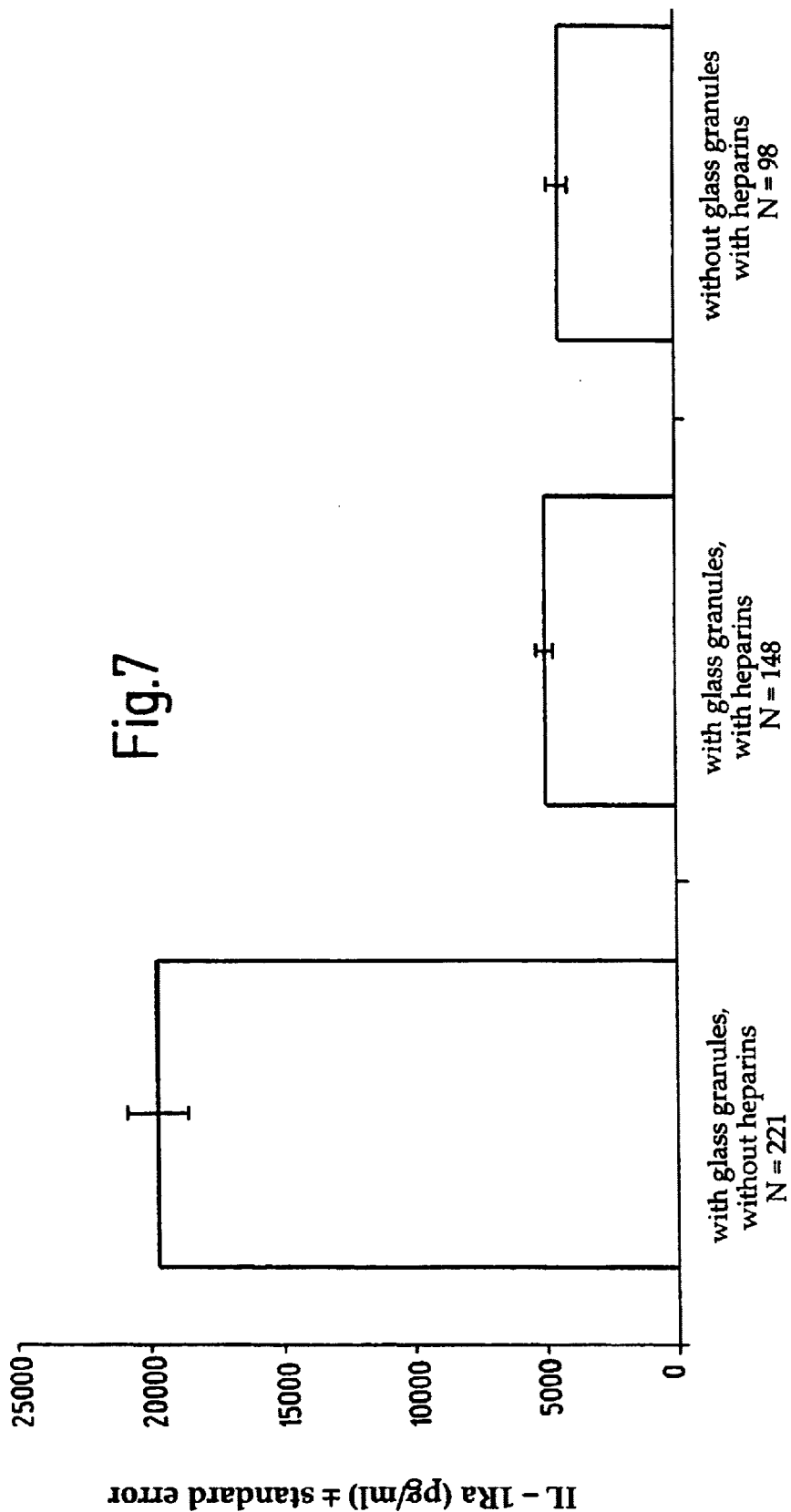

FIG. 7 is a bar graph showing IL-1Ra production in a glass syringe with and without glass granules and with and without heparin in a group of patients. IL-1Ra level in picograms per milliliter is shown on the Y axis, plus or minus standard error. The bars on the X-axis show IL-1Ra levels in a glass syringe (1) with glass granules, without heparin, N=96, (2)with glass granules, with heparin, N=148, and (3) without glass granules, with heparin, N=98 as discussed below.

Method
IL-1Ra production
Use of a glass syringe as described in example 1 Measurements on a group of orthopedic patients
Glass spheres
Roth, treated with chromosulphonic acid, washed and
    autoclaved
Result
IL-1Ra can be produced in a glass syringe both with and without glass granules and with and without heparin, but the efficiency of IL-1Ra production with glass granules and without heparin is significantly higher.

Figure 8:
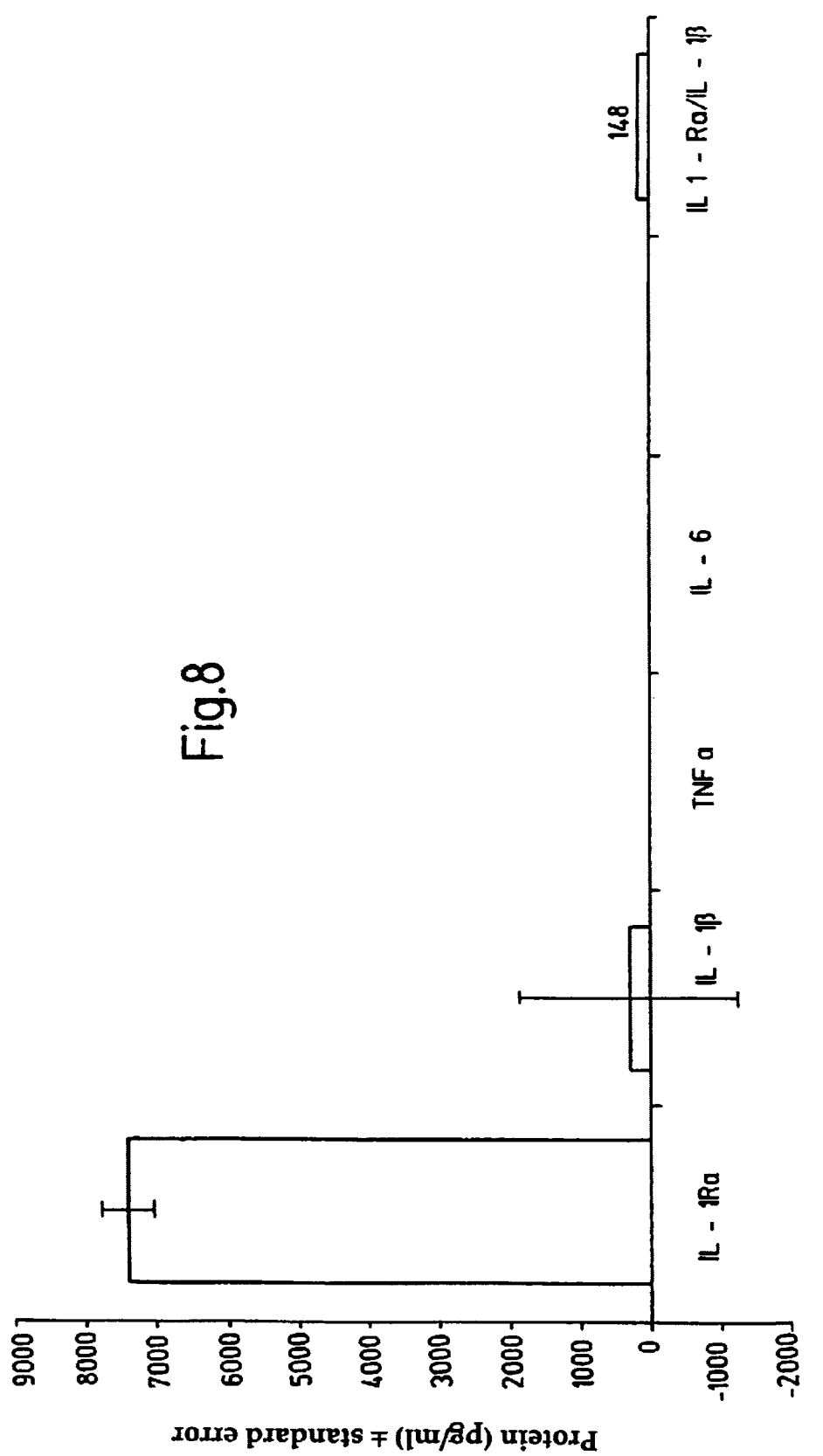

FIG. 8 is a bar graph showing protein production using a glass syringe with glass granules in a group of patients. Protein level (IL-1Ra, IL-1β, TNF α, IL-6) in picograms per milliliter is shown on the Y axis, plus or minus standard error. The bars on the X-axis show IL-1Ra, IL-1β, TNF α, IL-6, and both IL-1Ra and IL-1β levels as discussed below.

Method
Protein production
Use of a glass syringe as described in example 1 Measurements on a group of orthopedic patients
Glass spheres
Roth, treated with chromosulphonic acid, washed and
    autoclaved
TNFa
tumor necrosis factor alpha
IL-6
interleukin 6

ELISA
The IL-1, TNFa and IL-6 concentrations were determined using a Kombo-Kit from R&D
Result
Using the described method there is specific production of IL-1Ra. TNF-alpha and IL-6 production were undetectable. IL-1β is also produced in small quantities. Since the IL-1Ra:IL-1β ratio, which is expected ought to be more than 100 for a clinical therapeutic effect of the produced IL-1Ra (W. P. Arend et al., 1998, Annu. Rev. Immo. 16 m 27–55) averages 148, the autologously produced IL-1Ra is therapeutically valuable.

Figure 9:
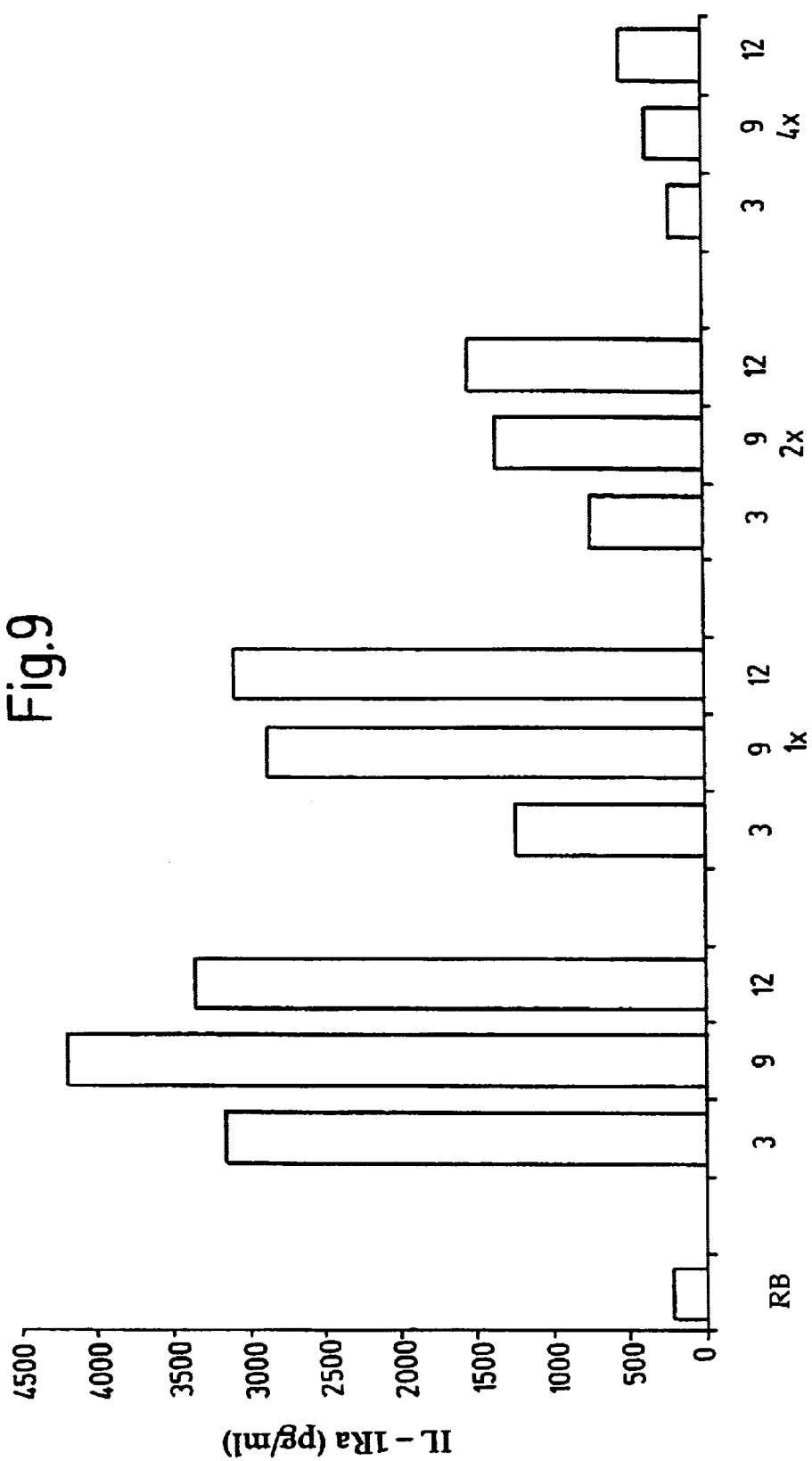

FIG. 9 is a bar graph showing IL-1Ra production using a microtiter plate with various amounts of glass granules and with various blood concentrations. IL-1Ra level in picograms per milliliter is shown on the Y axis, plus or minus standard error. The bars on the X-axis show IL-1Ra levels in a reaction blank (RB) or with 3, 9 or 12 glass spheres per well in heparinized blood at 1X, 2X, and 4X dilutions as discussed below.

Method
IL-1Ra production
Use of a microtiter plate as described in example 6. A difference is, however, that there was not addition of 1 ml of heparinized whole blood but addition of sufficient heparinized whole blood for the final volume to be 1 ml.
Glass spheres
Duran, treated with chromosulphonic acid, washed and
    autoclaved
3, 9, 12=addition of 3, 9 or 12 spheres
1×, 2×, 4×=heparinized whole blood diluted 1×, 2× or 4× with RPMI 1640
RB
Reaction blank, IL-1Ra concentration on removal (before IL-1Ra production) in undiluted blood
Result
With every blood dilution an increase in the amount of glass granules leads to an increase in IL-1Ra production. A maximum for IL-1Ra production is determined by the ratio between the number of spheres and the amount of blood, and between the glass surface area and the blood cell count.

Figure 10:
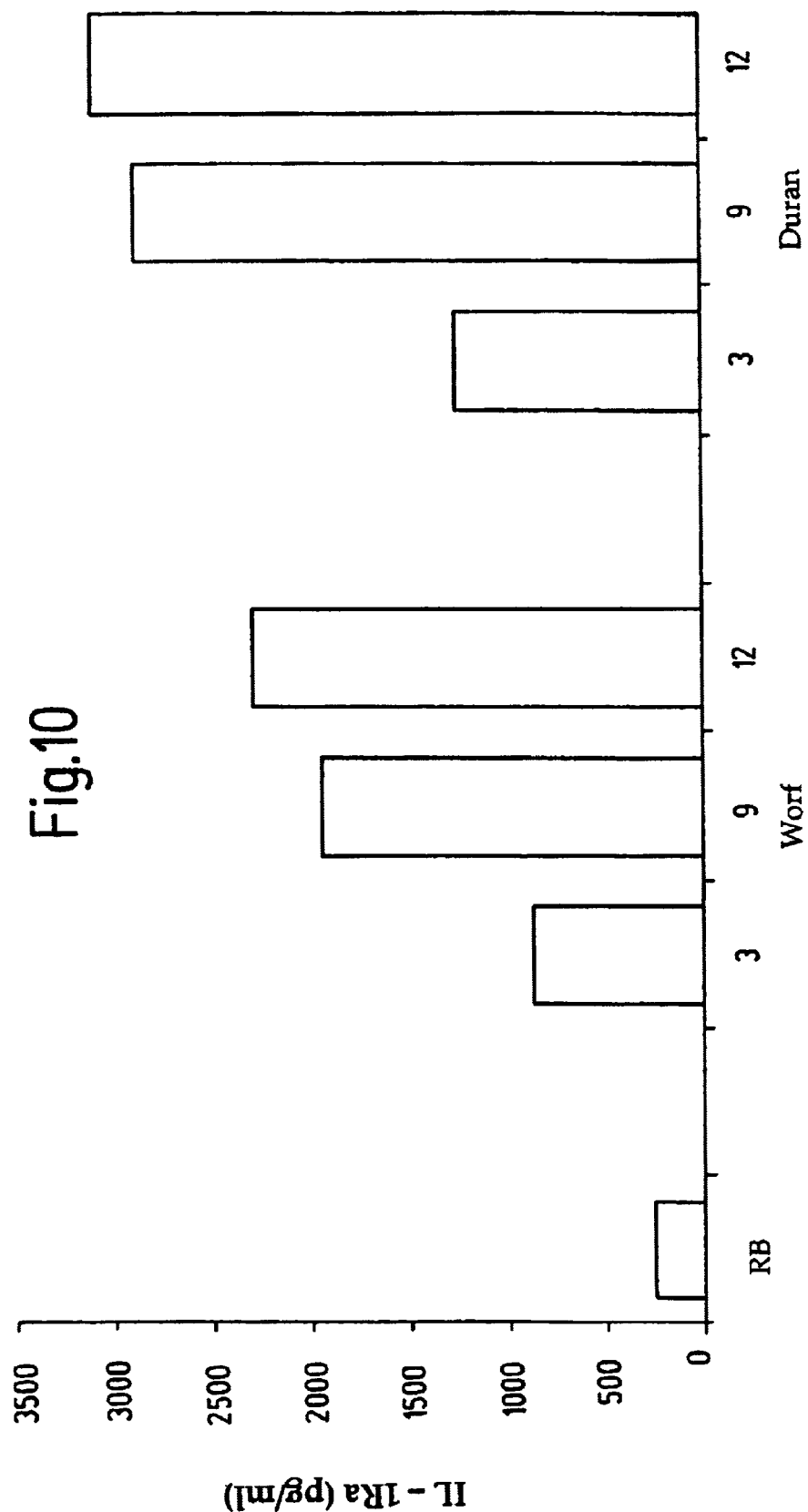

FIG. 10 is a bar graph showing IL-1Ra production using a microtiter plate with various amounts of glass granules and two types of glass granules. IL-1Ra level in picograms per milliliter is shown on the Y axis, plus or minus standard error. The bars on the X-axis show IL-1Ra levels (1) in a glass syringe with glass granulesn without heparin, N=96, (2) with glass granules, with heparin, N=148, and (3) without glass granules, with heparin, N=98 as discussed below.

Method
IL-1Ra production
Use of a microtiter plate as described in example 6
Glass spheres
Duran or Worf, treated with chromosulphonic acid, washed and autoclaved
3, 9, 12=addition of 3, 9 or 12 spheres
RB
Reaction blank, IL-1Ra concentration on removal (before IL-1Ra production)
Result
Increasing the number of spheres or the glass surface area leads to higher IL-1Ra production both with soda lime glass (Worf as example) and with borosilicate glass (Duran as example).

Figure 11:
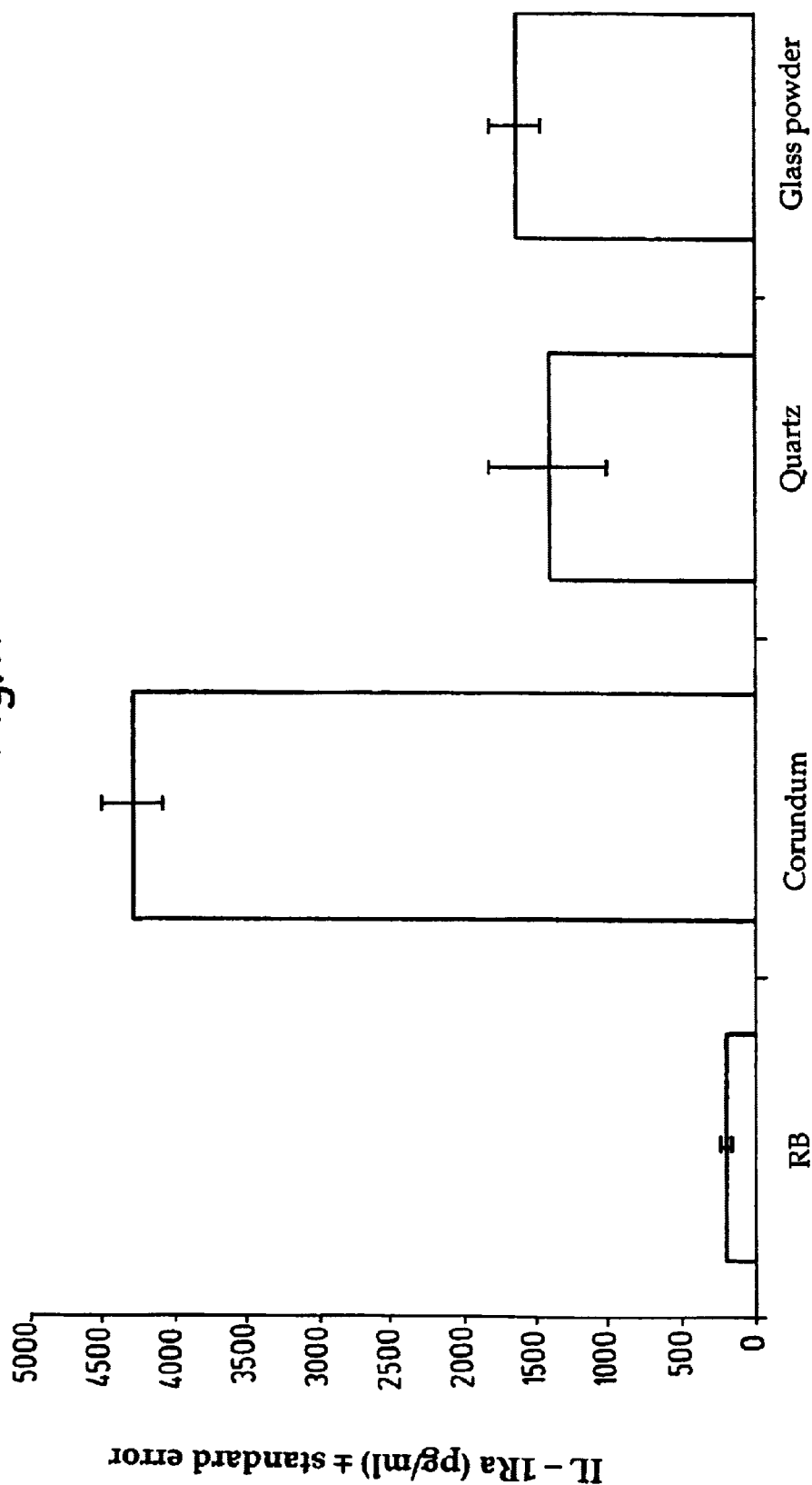

FIG. 11 is a bar graph showing IL-1Ra production using a microtiter plate with various amounts of glass granules and two types of glass granules. IL-1Ra level in picograms per milliliter is shown on the Y axis, plus or minus standard error. The bars on the X-axis show IL-R1a levels in a glass syringe (1) in a reaction blank (RB) (2) with corundum, (3) with quartz, and (4) with glass powder as discussed below.

Method
IL-1Ra production
Use of a microtiter plate as described in example 6
Glass spheres
Duran, treated with chromosulphonic acid, washed and autoclaved
RB
Reaction blank, IL-1Ra concentration on removal (before IL-1Ra production)
Corundum
alpha Al2O3 suspension
Quartz
Quartz sand, 220 mg/ml
Glass powder
0.2 mg/ml
Result The addition of silicate oxides or aluminum oxides, which are constituents of the glass granules described (see technical data for the glass granules), in the form of corundum or quartz sand leads to high IL-1Ra production.

Figure 12:
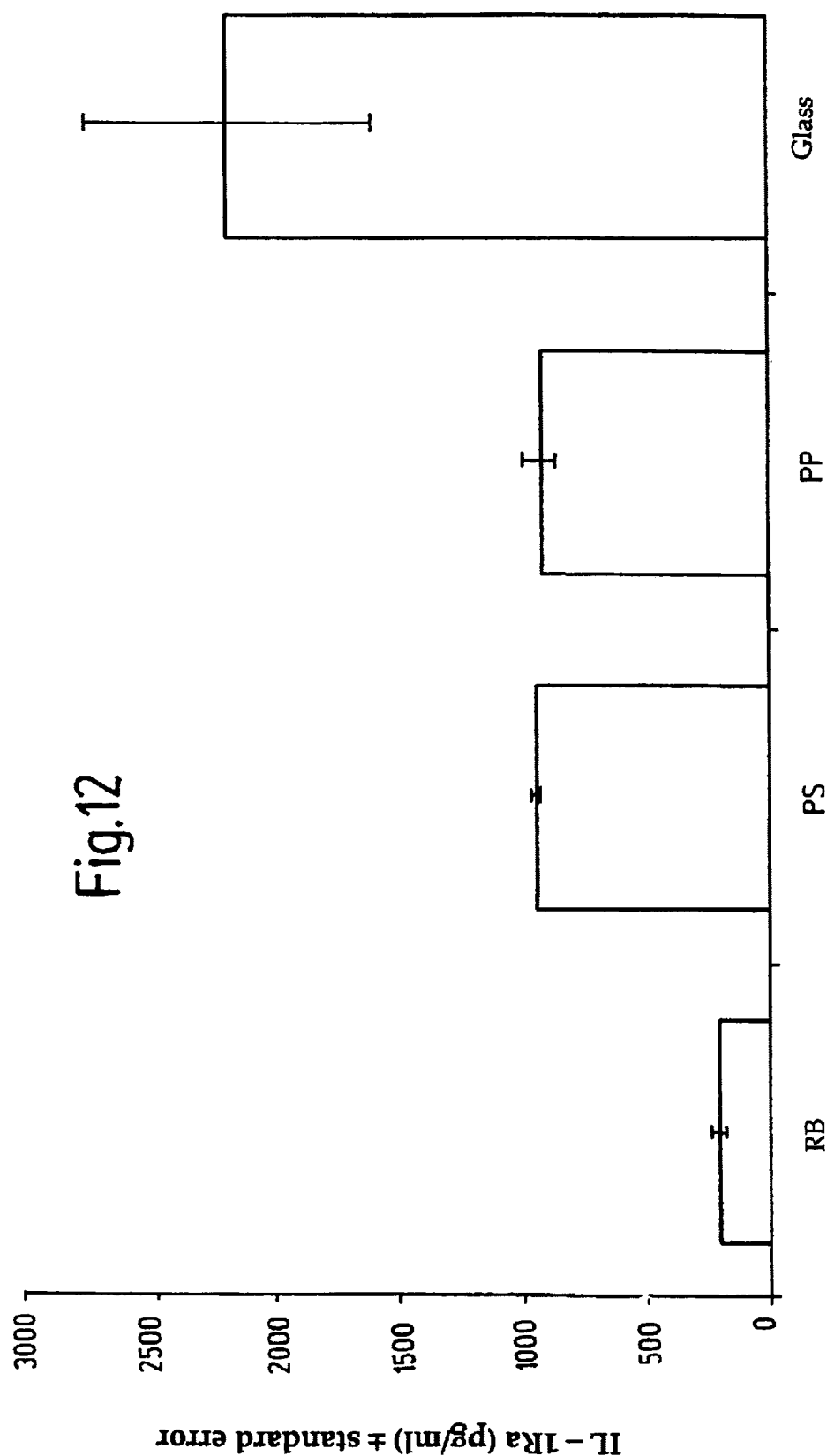

FIG. 12 is a bar graph showing IL-1Ra production under different container materials. IL-1Ra level in picograms per milliliter is shown on the Y axis, plus or minus standard error. The bars on the X-axis show IL-1Ra levels in (1) a reaction blank (RB), (2) with PS as a container material, (3) with PP as a container material, and (4) with glass as a container material as discussed below.

Method
IL-1Ra production
Use of a microtiter plate as described in example 6
Glass spheres
Duran, treated with chromosulphonic acid, washed and autoclaved
RB
Reaction blank, IL-1Ra concentration on removal (before IL-1Ra production)
PS
Polystyrene microtiter plate (from Nunc, Art. No. 150687)
PP
Polypropylene reaction vessel (from Sarsted, Art. No. 62/554.502)
Glass
Commercially available reaction vessel, autoclaved
Result IL-1Ra can be produced both in glass and in plastic containers, but the efficiency of IL-1Ra production in glass containers is significantly higher.

Figure 13:
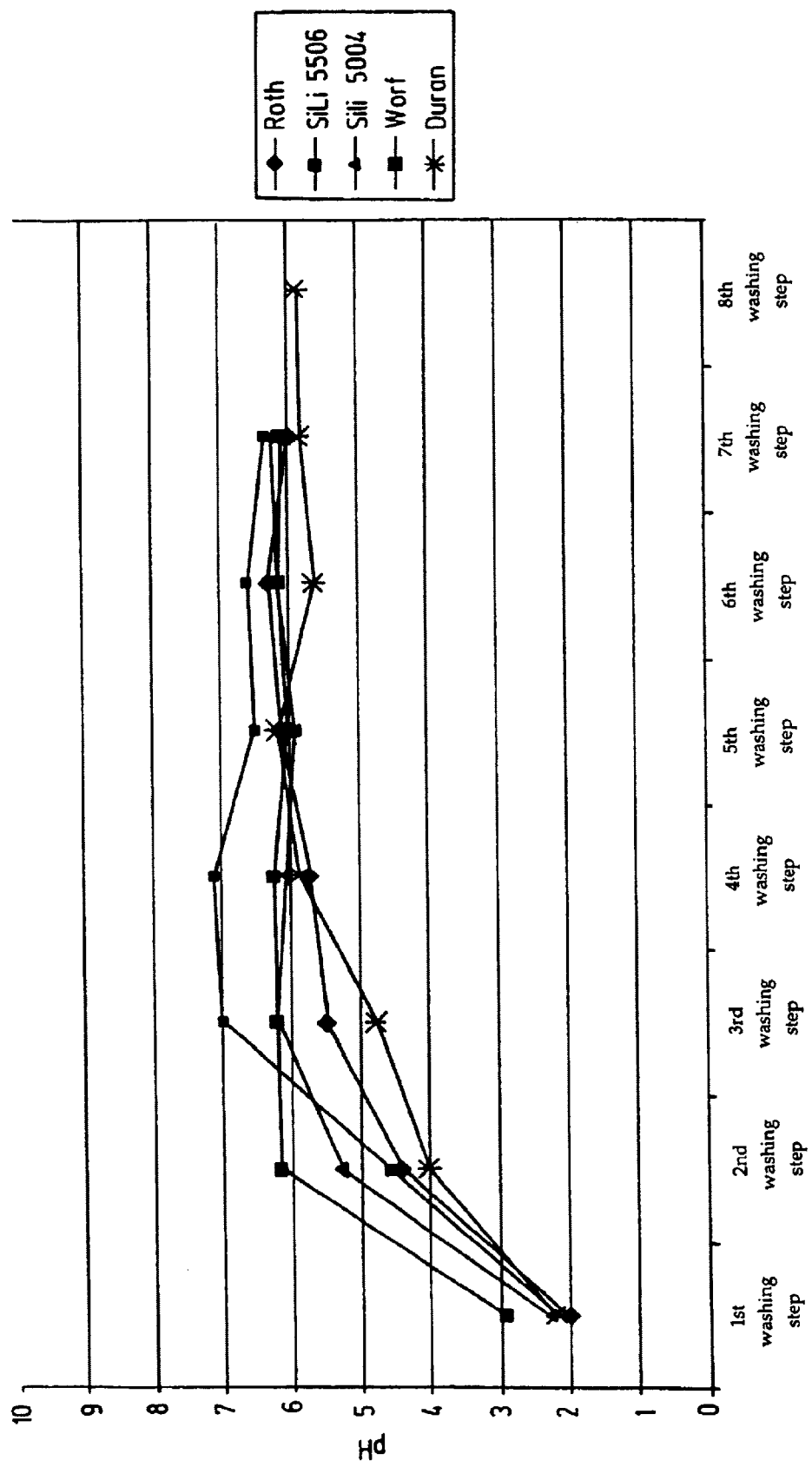
FIGS. 13 and 14 show the corrosive agent employed is completely removed by washing the syringe.

FIG. 13 shows the pH in the washing water after chromosulphonic acid treatment of glass granules. As shown in FIG. 13, various glass granules were used (Roth, SiLi 5506, SiLi 5504, Worf, and Duran). See Technical data of the glass granules table below for detailed information regarding glass granules.

Method
Glass spheres
All the listed spheres were treated with chromosulphonic acid; the pH was determined using a pH meter after each washing step Ultrapure water (Biochrom ultrapure water Art. No. L 0040), pH between 6.0 and 6.5, was used for washing
Result It was possible to wash away all acid residues for all the spheres described after the chromosulphonic acid treatment.

Figure 14:
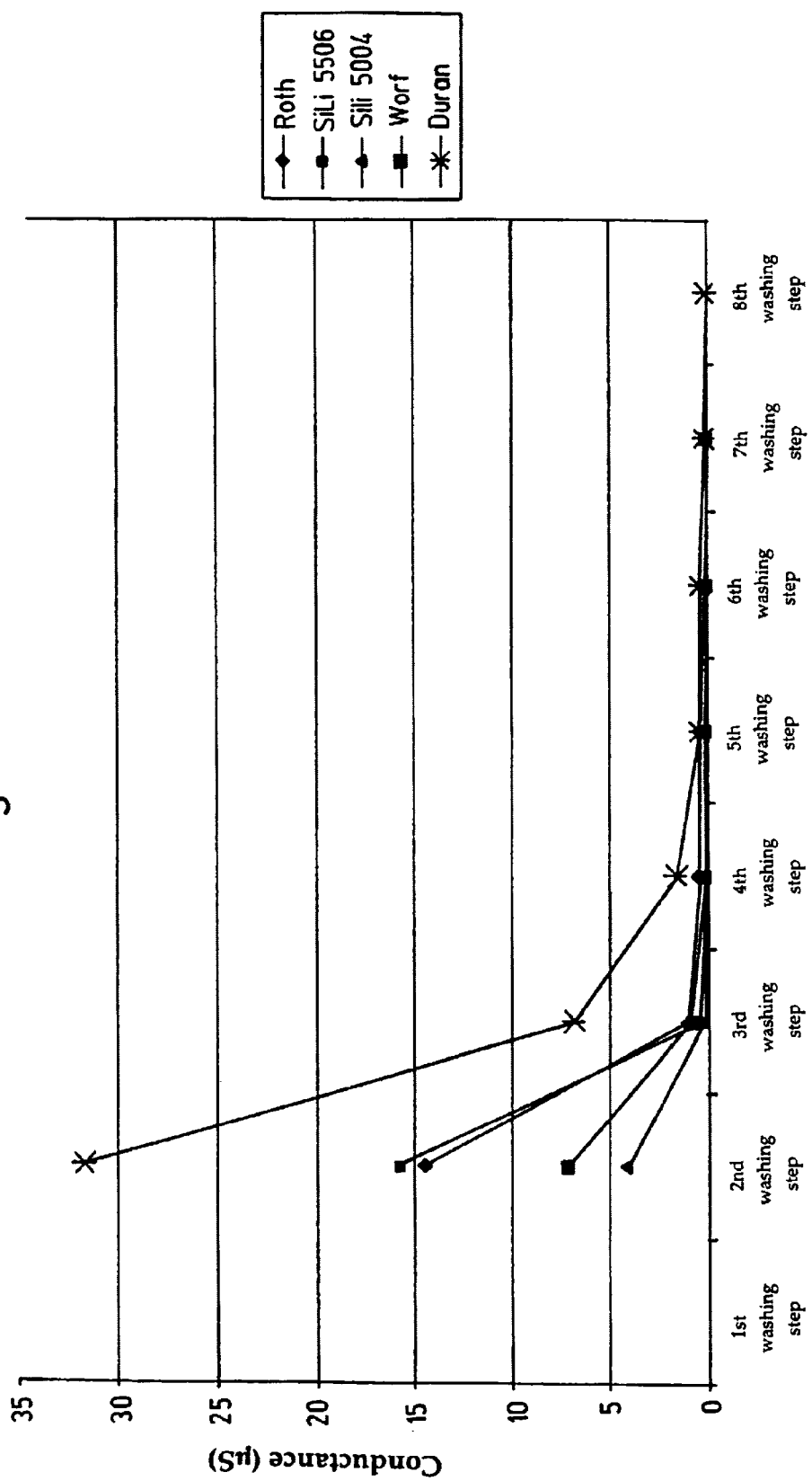

FIG. 14 shows the conductance in the washing water after chromosulphonic acid treatment of the glass granules. Various glass granules were used (Roth, SiLi 5506, SiLi 5004, Worf, and Duran) as discussed below.

Method
Glass spheres
All the listed spheres were treated with chromosulphonic acid, and then the conductance of the washing water was determined after each washing step using a conductance meter
Ultrapure water (Biochrom ultrapure water, Art. No. L 0040), conductance 0 $\mu$S, was used for washing
Result After chromosulphonic acid treatment and washing it was not possible to detect any leachates for any of the spheres described. It is thus possible to preclude IL-1Ra induction by possible leachates with pyrogenic activity.

Technical Data of the Glass Granules

| 1.1 Roth | |
|---|---|
| Size | 2.85–3.3 |
| Material | Chem. comp. see below |
| Chem. composition (%) | |
| SiO2 | 68 |
| CaO | 3 |
| BaO | 6 |
| K2O | 8 |
| Na2O | 10 |
| Al2O3 | 1 |
| B2O3 | 2 |
| Lead-free | |
| 1.2 SiLi 5506/89-6 | |
| Size | 2.3–2.5 mm |
| Material | Borosilicate glass |
| Treatment | 1. Grinding method |
| | 2. Polishing method |
| Chem. composition (%) | |
| SiO2 | 82 |
| Na2O | 2 |
| Al2O3 | 2 |
| B2O3 | 14 |
| Specific gravity (kg/dm3) | 223 |
| Mohs hardness | 7 |
| Coefficient of linear expansion (20–300° C.) | 325 |
| Hydrolysis class (DIN ISO 719) | 1 |
| Acid class (DIN 12116) | 1 |
| Alkali class (DIN ISO 695) | 2 |
| Transformation temperature (° C.) | 530 |
| 1.3 SiLi 5004/99-5 | |
| Size | 2.5 mm |
| Material | Soda lime glass |
| Treatment | Pressing method |
| Chem. composition (%) | |
| SiO2 | 67 |
| Na2O | 16 |
| CaO | 7 |
| Al2O3 | 5 |
| B2O3 | 3 |
| MgO | 2 |
| PbO | Free |
| Mohs hardness | >=6 |

-continued

1.4 Worf

| | |
|---|---|
| Size | 2 to 3.5 mm |
| Material | Soda lime glass |
| Treatment | Polished and thermally hardened |
| Chem. composition (%) | |
| $SiO_2$ | 65 |
| $Na_2O$ | 16 |
| CaO | 7 |
| $Al_2O_3$ | 5 |
| $B_2O_3$ | 3 |
| MgO | 2 |
| Lead content | Zero |
| Density (g/dm3) | 2.54 |
| Mohs hardness | 6 |
| Hydrolysis class | 3 |
| Deformation temperature (° C.) | 530 +/− 10 |

1.5 Duran

| | |
|---|---|
| Size | 2 to 3.5 mm |
| Material | Borosilicate glass |
| Treatment | 1. grinding method |
| | 2. polishing method |
| Chem. composition (%) | |
| $SiO_2$ | 81 |
| $Na_2O + K_2O$ | 4 |
| $Al_2O_3$ | 2 |
| $B_2O_3$ | 13 |
| Density (g/dm3) | 2.23 |
| Coefficient of linear expansion (20–300° C.) | 3.25 |
| Hydrolysis class (DIN ISO 719) | 1 |
| Acid class (DIN 12116) | 1 |
| Alkali class (DIN ISO 695) | 2 |
| Transformation temperature (° C.) | 525 |

What is claimed is:

1. A method for producing IL-1Ra in a syringe, wherein the syringe is filled with blood from a mammal and incubated in the syringe for a sufficient time and at a sufficient temperature to produce IL-1Ra in said blood.

2. The method according to claim 1, wherein the syringe comprises glass plastic, corundum and/or quartz.

3. The method according to claim 2, wherein the plastic comprises polystyrene, polyvinyl chloride, polyethylene or polypropylene.

4. The method according to claim 1, wherein the syringe has an internal structure which has been modified.

5. The method according to claim 1, wherein the syringe has an internal structure modified by means of a corrosive agent.

6. The method according to claims 4 or 5, wherein the internal structure of the syringe is formed by its internal surface having formations that enlarge the surface area.

7. The method according to claim 6, wherein the internal structure is formed by beads, spheres, gels, wool, powder, granules or particles made of glass, plastic, corundum and/or quartz in the syringe.

8. The method as claimed in claim 5, wherein the corrosive agent comprises an alkali or acid.

9. The method according to claim 8, wherein said corrosive agent is chromosulphonic acid.

10. The method according to claim 1, wherein the blood is incubated in the syringe from about 12 to 72 hours.

11. The method according to claim 1, wherein the blood is incubated in the syringe at about 20 to 37 degrees centigrade.

12. The method according to claim 1, wherein the syringe has an internal structure coated with an anticoagulant.

13. The method according to claim 12, wherein said anticoagulant is selected from the group consisting of heparin, citrate, EDTA, CPDM, and CPDA.

* * * * *